United States Patent [19]

van der Zel

[11] Patent Number: 4,937,928
[45] Date of Patent: Jul. 3, 1990

[54] METHOD OF MAKING A DENTAL CROWN FOR A DENTAL PREPARATION BY MEANS OF A CAD-CAM SYSTEM

[75] Inventor: Joseph M. van der Zel, Kapberg, Netherlands

[73] Assignee: Elephant Edelmetaal B.V., Hoorn, Netherlands

[21] Appl. No.: 253,772

[22] Filed: Oct. 5, 1988

[30] Foreign Application Priority Data

Oct. 7, 1987 [NL] Netherlands ............... 8702391

[51] Int. Cl.$^5$ .............................................. B23P 13/00
[52] U.S. Cl. ..................................... 29/160.6; 409/80; 433/223
[58] Field of Search ............... 29/160.6; 409/79, 80, 409/82, 84; 433/202.1, 206, 207, 204, 205, 208, 213, 218, 223

[56] References Cited

U.S. PATENT DOCUMENTS

| | | | |
|---|---|---|---|
| 3,502,466 | 3/1970 | Vickery | 29/160.6 |
| 3,861,044 | 1/1975 | Swinson | 433/218 |
| 4,324,546 | 4/1982 | Heitlinger et al. | 433/51 |
| 4,411,626 | 10/1983 | Becker et al. | 433/223 |
| 4,556,389 | 12/1985 | Ueno et al. | 433/208 |
| 4,558,977 | 12/1985 | Inoue et al. | 409/80 |
| 4,575,805 | 3/1986 | Moermann et al. | 433/204 |

FOREIGN PATENT DOCUMENTS

| | | |
|---|---|---|
| 2186483 | 6/1984 | Australia . |
| 0110797 | 6/1984 | European Pat. Off. . |
| 1575661 | 7/1969 | France . |
| 1223007 | 2/1971 | United Kingdom . |

Primary Examiner—Carl E. Hall
Assistant Examiner—I. Cuda
Attorney, Agent, or Firm—Stevens, Davis, Miller & Mosher

[57] ABSTRACT

A method of making a dental crown for a dental preparation by means of a CAD-CAM system. In the method, first a model of the dental preparation is made from a refractory material under the control of the CAD-CAM system. Subsequently, at least one layer of a material suitable for dental crowns is applied to the model. The layer is sintered during or after its application, and is then ground under the control of the CAD-CAM system until a predetermined shape is obtained. Finally the refractory material is removed.

11 Claims, 1 Drawing Sheet

METHOD OF MAKING A DENTAL CROWN FOR A DENTAL PREPARATION BY MEANS OF A CAD-CAM SYSTEM

This invention relates to a method of making a dental crown for a dental preparation by means of a CAD-CAM system.

A method of this kind is described in Dentist News, January 1987, pages 16–18. This known method aims at simplifying the labour-intensive manufacture of dental crowns by using computer-aided design techniques, the so-called CAD-CAM techniques. To that end, a 3-dimensional photo is taken of the preparation made by a dentist in the patient's mouth, by means of a laser-optical probe, i.e. the stump of tooth material over which the crown is to be placed, and of the teeth surrounding the preparation. This photo is digitized and supplied to the CAD-CAM system, displaying the 3-dimensional picture on a viewing screen. The dental mechanic or the dentist is now in a position to select the most suitable tooth form from a plurality of tooth forms stored in the CAD-cam system and by means of the operating panel of the system, to manipulate the image of the selected tooth form projected over the image of the preparation until an optimum positioning and fit of the crown is obtained. The digital data concerning the crown thus formed are supplied to a numerically controlled milling machine operating in three dimensions, which cuts the crown on the basis of the digital data supplied from a solid piece of metal or workable glass suitable for dental mechanics.

EP-A-0025911 describes a method of manufacturing a crown, in which a tooth stump is optically measured with the aid of a computer, after which a model of the tooth stump is made by means of the data obtained by means of a computer-controlled cutter. Subsequently, the crown is formed by hand on this stump from wax, which crown is again measured with the aid of the computer after which the cutter cuts the crown with the aid of the computer from a solid block of material.

The known method has a number of drawbacks. In the first place, the starting material is metal or glass, which does not permit optimum dental restoration, because the glass usable for dental restoration, and in particular the metal, has a color that deviates strongly from the natural color of teeth. In the second place, there is a substantial loss of material, because a solid piece of material is the starting point, which is undesirable, in particular in the case of crowns from precious metals. Finally, the crown may become too loose, due to the unavoidable wear of the cutting tool, so that it no longer fits.

It is an object of the present invention to provide a method devoid of all these drawbacks and with which in particular a dental crown can be made, which, as regards color, can be conformed optimally to the color of the teeth already present.

To that end, the present invention provides a method of the above described type, in which under the control of the CAD-CAM system a model of the dental preparation is made from a refractory material, to which model there is applied at least one layer of a material suitable for dental crowns, said layer being subsequently sintered and ground under the control of the CAD-CAM system until a predetermined shape is obtained, after which the refractory material is removed.

The present invention is based on the insight that the loss of valuable material suitable for dental restoration can be substantially avoided by applying one or more layers to a model made through CAD-CAM techniques of the stump prepared by the dentist in the patient's mouth (referred to herein as the "preparation"), which layer or layers are sintered onto the refractory, relatively inexpensive model, after which the layer or layers are ground to a desired shape under the control of the CAD-CAM system. The quantity of material to be ground off may be small, while the largest gain in material is obtained due to the fact that no cavity need be cut to receive the preparation, which has to be done in the known method. A further advantage is that according to the present invention only the shape of the model of the dental preparation need be cut from refractory material. This model consists of a relatively soft material, preferably fine-grained MgO, so that wear of the cutting tool is minimal. Any wear of the cutting tool will moreover result in a, true, slightly too large, but still well usable restoration.

With the method according to the present invention, it is possible to make on the model of a dental preparation, a crown in one or more layers of metal, a ceramic material or a combination of these two materials.

According to a preferred embodiment of the present invention, a first layer consists of a known dental alloy suitable for firing porcelain onto it, a second layer of opaque porcelain, a third layer of a dentin porcelain and a fourth layer of a porcelain suitable to form a cutting mass. Each of these layers is sintered simultaneously with, or after, its application to the model of the dental preparation or to the preceding layer and subsequently ground under the control of the CAD-CAM system to the contour determined by the system.

With the method according to the preferred embodiment of present invention, dental crowns can be made which, as regards color, cannot be distinguished from the teeth already present.

BRIEF DESCRIPTION OF THE DRAWINGS

The present invention will now be further described with reference to the accompanying drawing, in which.

DETAILED DESCRIPTION OF THE DRAWINGS

Figures 1A, 1B:
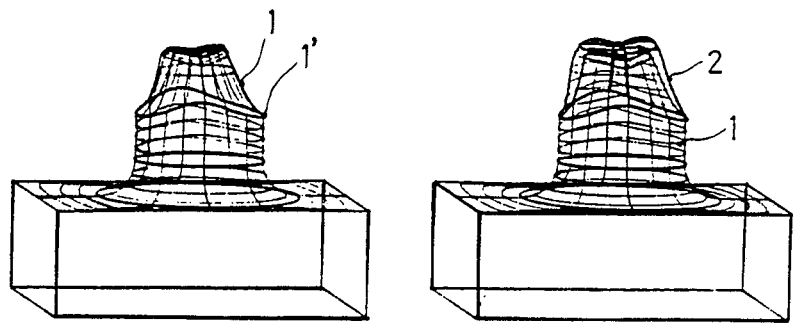
FIGS. 1a–1e show the successive steps of the manufacture of a dental crown for a premolar by means of the CAD-CAM system.

FIG. 1a shows a 3dimensional representation of a dental preparation 1 of a patient, displayed, by means of a CAD-CAM system, on a viewing screen the shape of which preparation has been picked up in known manner in the patient's mouth by means of a laser-optical probe, subsequently digitized and supplied to the CAD-CAM system. A model conforming to the shape 1 is cut from a refractory material by means of a numerically controlled 3-dimensionally operating cutter, under the control of the CAD-CAM system. The refractory material chosen is preferably a material having a thermal coefficient of expansion that corresponds as closely as possible with that of the dental alloy to be applied in the next step. Preferably, the refractory material consists of magnesia, possibly with binding agents, because magnesia is both refractory and has a linear thermal coefficient of expansion that exhibits substantial resemblance with that of the conventional dental alloys.

Subsequently, as shown in FIG. 1b, there is applied to the model of the dental preparation 1, a metal layer 2 from a known per se metal alloy suitable for firing porcelain onto it. Such an alloy may consist of 81% Pd, 10% Cu and 9% Ga or of 84% Au, 10% Pt, 5% Pd and 1% In. The application of the metal layer is effected preferably by spraying metal powder having a grain size smaller than 60 micrometers and a bulk density larger than 70% of the theoretical density of the alloy. Known techniques for spraying metal powder are plasma jetting, laser sintering, flame spraying or pneumatic spraying. In plasma jetting and laser sintering, the metal layer is sintered directly onto the refractory model 1, while in the other application methods this is effected afterwards.

Subsequently, the metal layer, sprayed a bit too thickly, is ground to the desired shape and thickness under the control of the CAD-CAM system, preferably by means of a numerically controlled, 3-dimensionally operating grinding machine. These parameters depend upon the strength of the material used and are calculated by means of the CAD-CAM computer. The thickness of the metal layer at the top face of the crown is determined e.g. at ⅓ of the total thickness, while the side faces taper to a thickness =0 near the lower edge 1' of the crown to be formed.

Figures 1C, 1D:
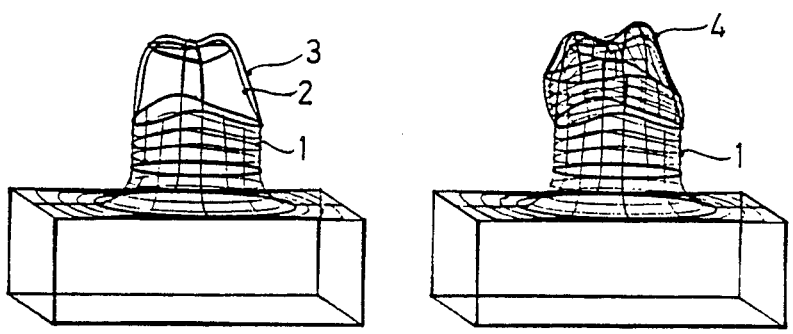

FIG. 1c shows a layer 3 of opaque porcelain, aiming at rendering the metal layer invisible for the purpose of an optimum color matching. This porcelain layer can be applied and sintered with the same techniques as the metal layer 2 and can also be ground similarly to the metal layer until the shape determined by the CAD-CAM system is attained. Layer 3 may consist of 53% $SiO_2$, 12% $Al_2O_3$, 9% $K_2O$, 2% $Na_2O$, 1% BaO and 23% $SnO_2$, the latter material ensuring the actual opaqueness of the porcelain layer.

FIG. 1d shows a layer 4 of dentin porcelain determining the eventual color of the crown. This layer, too, is applied and machined similarly to metal layer 2 and opaque porcelain layer 3. Naturally, the contour to which this layer is ground is again larger than the contour to which layer 3 had been ground. The composition of the dentin porcelain may be 65% $SiO_2$, 18% $Al_2O_3$, 12% $K_2O$, 3% $Na_2O$, 1.5% BaO and 0.5% coloring agent.

Figure 1E:
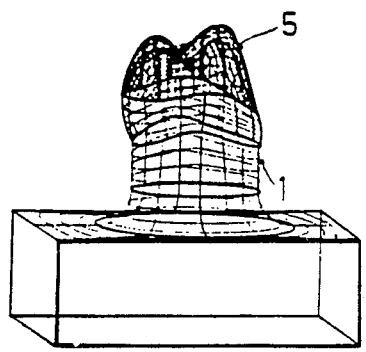

Finally, FIG. 1e shows how a cutting mass layer 5 is applied to the crown as a finishing layer. For this layer, too, the same application and machining techniques are employed, with layer 5 being ground until the final shape of the crown determined with the CAD-CAM system is obtained. The cutting mass layer may have the same composition as the dentin porcelain layer 4, but contains less coloring agent, in order that said layer is more translucent, which enhances the naturalness of the color of the crown.

It will be clear that only one possibility has been described above to provide a dental crown by means of the method according to the present invention and that a great many variants are possible without departing from the scope of the present invention as regards the materials to be used, the methods of application and machining techniques.

I claim

1. A method of making a dental crown for a dental preparation by means of a CAD-CAM system wherein under the control of the CAD-CAM system a model of the dental preparation is made from a refractory material, to which model successively two or more layers of a material suitable for dental crowns are applied, each layer being sintered during or after its application and being ground after the sintering treatment and before the next layer is applied, which grinding treatments are effected under the control of said CAD-CAM system until a shape determined by said system is obtained, after which the refractory material is removed.

2. A method as claimed in claim 1, characterized in that the refractory material is MgO and that the model is cut under the control of the CAD-CAM system to obtain the shape of the dental preparation.

3. A method as claimed in claim 2, characterized in that the layers are applied by means of plasma jetting.

4. A method as claimed in claim 1, characterized in that four layers are applied to the model of the dental preparation, the first layer being a metal layer of a dental alloy, the second layer an opaque porcelain layer, the third layer a dentin porcelain layer and the fourth layer a cutting mass layer.

5. A method as claimed in claim 4, characterized in that the dental alloy is made up of a metal powder having a grain size smaller than 60 micrometers and a bulk density larger than 70% of the theoretical density of the alloy.

6. A method as claimed in claim 5, characterized in that the layers are applied by means of plasma jetting.

7. A method as claimed in claim 4, characterized in that the layers are applied by means of plasma jetting.

8. A method as claimed in claim 1, characterized in that the layers are applied by means of pneumatic spraying.

9. A method as claimed in claim 1, characterized in that the layers are applied by means of plasma jetting.

10. A method as claimed in claim 1, characterized in that the layers are applied by means of flame spraying.

11. A method as claimed in claim 1, characterized in that the layers are applied by means of laser sintering.

* * * * *